(12) United States Patent
Sonnenborg

(10) Patent No.: US 8,874,185 B2
(45) Date of Patent: Oct. 28, 2014

(54) METHOD FOR DETERMINING ELECTRICAL BIOPOTENTIALS

(71) Applicant: Finn Albert Sonnenborg, Frederikssund (DK)

(72) Inventor: Finn Albert Sonnenborg, Frederikssund (DK)

(73) Assignee: Ambu A/S, Ballerup (DK)

( * ) Notice: Subject to any disclaimer, the term of this patent is extended or adjusted under 35 U.S.C. 154(b) by 0 days.

(21) Appl. No.: 13/690,553

(22) Filed: Nov. 30, 2012

(65) Prior Publication Data

US 2013/0131481 A1    May 23, 2013

Related U.S. Application Data

(62) Division of application No. 11/922,562, filed as application No. PCT/DK2006/000369 on Jun. 22, 2006, now abandoned.

(30) Foreign Application Priority Data

Jun. 22, 2005   (DK) ................. PCT/DK2005/000420

(51) Int. Cl.
*A61B 5/04* (2006.01)
*A61B 5/00* (2006.01)
*A61B 5/0408* (2006.01)
*A61B 5/0402* (2006.01)

(52) U.S. Cl.
CPC ................ *A61B 5/04* (2013.01); *A61B 5/0006* (2013.01); *A61B 2560/0412* (2013.01); *A61B 5/04085* (2013.01); *A61B 5/04028* (2013.01)
USPC ........... 600/382; 600/372; 600/386; 600/388; 600/509

(58) Field of Classification Search
USPC ......... 600/372, 374, 382, 384, 386, 391, 393, 600/395–396, 508–509
See application file for complete search history.

(56) References Cited

U.S. PATENT DOCUMENTS

| | | | |
|---|---|---|---|
| 4,981,141 A * | 1/1991 | Segalowitz | 600/509 |
| 6,272,364 B1 * | 8/2001 | Kurnik | 600/345 |
| 7,206,630 B1 * | 4/2007 | Tarler | 600/509 |
| 7,742,807 B1 * | 6/2010 | Walls | 600/509 |
| 2002/0045836 A1 * | 4/2002 | Alkawwas | 600/509 |

* cited by examiner

Primary Examiner — Linda Dvorak
Assistant Examiner — Brian M Antiskay
(74) Attorney, Agent, or Firm — Finnegan Henderson Farabow Garrett & Dunner LLP

(57) ABSTRACT

A set of electrodes suitable for being attached to the skin of an animal or human being at locations normally used for attaching single-lead electrodes with a single sensor point. The electrodes of the set of electrodes have at least three sensors arranged to define two linearly independent directions, which allows sensing corresponding electrical potential differences in the two directions. Signals representing sensed potential differences can be transmitted wirelessly or via conductors to a processing apparatus for being transformed into electrical potentials that approximate traditional potentials obtained with wired single-sensor electrodes. A method is also presented.

11 Claims, 2 Drawing Sheets

METHOD FOR DETERMINING ELECTRICAL BIOPOTENTIALS

PRIORITY INFORMATION

This application is a divisional of co-pending U.S. patent application Ser. No. 11/922,562, filed Mar. 23, 2009, which is a national stage entry of International Application No. PCT/DK2006/000369, filed Jun. 22, 2006, which claims priority from International Application No. PCT/DK2005/000420, filed Jun. 22, 2005, all of which are incorporated herein by reference.

FIELD OF THE INVENTION

The invention relates to sensing of electric surface potentials by means of electrodes attached to the skin of an animal or human being. Such uses include in particular electrocardiography (ECG), electroencephalography (EEG) and electromyography (EMG).

BACKGROUND

When measuring ECG, EEG and EMG a plurality of electrodes, each of which have a sensor, are attached to the skin of an animal or human patient. Each sensor on each electrode senses the electrical potential at a relatively small area—typically a few mm in diameter—on the skin immediately below the sensor. Usually an electrically conductive contact medium is used between the sensor and the skin. The sensed electrical potentials are transmitted through individual conductors to an apparatus, which measures, registers and/or evaluates the sensed potentials, e.g. by determining differences between electrical potentials at the electrodes and linear combinations thereof. Such systems have long been used for monitoring and diagnostic purposes.

U.S. Pat. No. 4,583,549 and others disclose an ECG electrode pad comprising a flexible sheet with a plurality of ECG electrodes positioned thereon to correspond with the anatomically correct placement for precordial ECG electrodes.

U.S. Pat. No. 5,724,984 discloses an electrode with a central sensor segment and several peripheral sensor segments arranged symmetrically around the central sensor segment.

U.S. Pat. No. 6,577,893 discloses an integrated wireless medical diagnosis and monitoring equipment with two or more electrodes and a wireless transmitter for transmitting sensed electrode signals.

US 2002/0045836 A1 discloses a method of calculating the standard ECG leads based on a number of smaller measurements. The method is based on arranging a set of sensors in a rectangle with the longitudinal axis along the standard ECG lead. The standard ECG lead measurement is calculated based on a number of assumptions.

U.S. Pat. No. 6,295,466 B1 discloses an electrode comprising three sensors arranged in orthogonal relationship. The output from the three sensors is combined in order to find a vector magnitude describing the magnitude of the change in the electric field at the sensors location. However, no information is provided with respect to the standard ECG or to the direction of the change of the field.

ECG signals originate from the coordinated activation and contraction of the heart muscles resulting in blood circulation through the body. The ECG signal starts at the SA node and initiates the contraction of the atrial myocardium resulting in the P wave, which travels down the centre line of the heart. The AV node and the bundle of His are activated, whereby the activation of the ventricles is initiated. First the septum (the muscle that separates the two ventricles) is activated, which results in the Q wave as the signal is travelling down the centre line of the heart. Then the free outer walls of the ventricles are activated, which results in the R and S waves. There the activation travels from the apex of the heart up the centre line, and completes the QRS complex. The T wave originates from the re-polarisation of the outer walls of the ventricles, actually travelling from the apex upright the centre line, but with inverted signal polarity, resulting in what appears to be a downward movement towards the apex. Finally, a small U wave can be found which originates from a late activation of the ventricles. The shape of the recorded ECG signal depends on the location of the electrodes and the polarity of the recording.

The ECG signal used in diagnostics originates from measuring the difference in the biopotential between different sites on the body. There are several different standards for recording/forming the ECG signal and these will not be discussed here. The reader is referred to any basic medical textbook. In the following, the three standard leads or limb leads (I, II, III) forming the Einthoven's triangle [10] are taken as an illustrative example. Traditionally, the electrode placements of the limb leads are on the right arm (RA), left arm (LA) and left leg (LL). In several clinical applications the limb electrodes are placed on the torso near the extremities without loss of information [5], [8].

The limb leads are defined as potential differences recorded between the three electrodes. Specifically they are:

$$I = V_{RA} - V_{LA}$$

$$II = V_{RA} - V_{LL}$$

$$III = V_{LA} - V_{LL}$$

where $V_{XX}$ is the potential recorded under electrode XX (eq. I).

Besides the primary standard limb leads, the unipolar limb leads, also called augmented leads, can be calculated from the same three potential recordings as the standard limb leads. Together, the standard limb leads and the unipolar limb lead form a vector system constructed of 6 vectors.

$$aVR = V_{RA} - (V_{LA} + V_{LL})/2$$

$$aVL = V_{LA} - (V_{RA} + V_{LL})/2$$

$$aVF = V_{LL} - (V_{RA} + V_{LA})/2$$

In traditional ECG recordings, ECG signals are recorded as the difference between two potentials at two different sites on the body. The voltage difference is measured relative to a reference point, which is taken as a "zero potential" on the body. This means that the signal is always in relation to a single common point on the body. This reference point can be a single site/electrode placed on a site of the body that is minimally influenced by the body potential of interest, or the reference can be one or several potentials/electrodes. This dependency on a reference point(s) limits the possibilities of transmitting the signal of a single electrode over a non-reference transmission line, e.g. wirelessly. Normally this would only be possible if a relation between at least two electrodes can be made, e.g. with a pair of wires connecting two electrodes to a transmitter.

Traditionally, each sensor has its own conductor that connects the sensor to the measuring and/or evaluating apparatus. With several electrodes and a corresponding number of individual conductors there is a risk of confusing the conductors and of connecting sensors to wrong inputs of the apparatus. A patient with a set of such electrodes attached has his/her mobility restricted by the length of the conductors. In equipment powered by AC mains power supply the electrodes must be extremely well isolated from the AC mains power supply in order to ensure patient safety.

In most currently available systems for telemetric monitoring of patients a set of electrodes are attached to the patient, where each electrode is connected via a conductor to a common transmitter carried by the patient. Such systems also have conductors that restrict the freedom and the mobility of the patient.

There is therefore a need for a disposable electrode, a method of measuring potential differences between different points on the body without the need for a common voltage between the points, and a system that allows wireless transmission of signals representing sensed potentials from each electrode. There is also a need for more detailed information on the electrical biopotential underneath the electrode, such as the direction of propagation of the biopotential.

SUMMARY OF THE INVENTION

The invention offers a solution to this problem by presenting a new type of electrode set, a new method for measuring an ECG signal and a new system for measuring an ECG signal The disposable electrode set of the current invention is suitable for being attached to the skin of an animal or human being at locations normally used for attaching single-lead electrodes with a single sensor point.

Each electrode in the electrode set comprises at least three sensors or sensing points. The at least three sensors are arranged to define two linearly independent directions. In this way, it is possible to measure an electrical potential difference in both of the two directions. Signals representing sensed potential differences can be transmitted wirelessly or via conductors to a processing apparatus for being transformed into electrical potentials that approximate traditional potentials obtained with wired single-sensor electrodes. Embodiments of methods for the transformation are disclosed later on in this specification.

With the method of the invention the electrical potential at the location of each electrode relative to the electrical potential at a reference position is determined or estimated based on the sensed potential differences between respective pairs of sensors of the electrodes. The electrical potentials can be determined as numerical values corresponding e.g. to the traditional ECG measurements with single-lead electrodes with a single sensor point, or the electrical potentials can be determined as vector values having two coordinates that define size (a numerical value) and direction, e.g. the direction of propagation of the sensed signal.

In one dimension the body potential can be regarded as a propagating signal, which will pass under the sensor points of an electrode at a given speed of propagation. Even though the action potentials originating from the heart muscle activity are placed "far" from the electrodes, the signal will propagate under the electrodes due to the volume conductivity of the rest of the body.

When two sensor points of an electrode are placed close together they will both sense the same wave, and the resulting differential between the two sensor points will be small, and a gradient in the direction of the centre line can be measured when the distance between the sensor points is known. Hereby a differentiation, in space and time, can be made of the passing body potential. In this case the body potential can be estimated via an integration of the measured signal. The integration results in an approximation of the size of the passing potential.

If the distance between the sensor points of the electrodes is large so that the entire potential wave can fit between the two sensor points, the recording would not function as a differential but as a full potential recording of the signal under the electrode. In this case, integration is not necessary.

Using two sensor points as above works for the one-dimensional space, where the two sensor points can be placed in such a way that the centre line of the sensor points is parallel to the direction in which the potential wave is moving. If the potential wave moves in a direction different form that of the centre line, a smaller potential difference will be measured, and if the potential wave moves perpendicular to the centre line of the two sensor points the sensor points will sense substantially the same signal, and the recorded difference between the two sensor points will be (almost) zero. Therefore the orientation of two sensor points is essential for the resulting recorded amplitude.

The invention provides an electrode with at least three sensors or sensor points arranged so that lines through the centres of respective pairs of sensors define at least two linearly independent, i.e. different, directions. In a preferred embodiment, the at least two linearly independent directions are perpendicular to each other. Measurements are taken using two pairs of sensors to obtain two corresponding potential differences representing vector coordinates of a two-dimensional vector corresponding to the two-dimensional gradient at any instant in time.

DETAILED DESCRIPTION OF THE INVENTION

Figure 1:
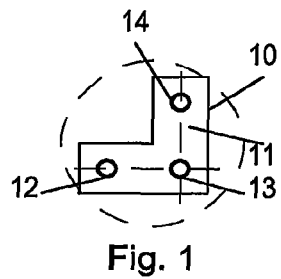
FIG. 1 shows an electrode with three sensors and a button-type connection to the individual sensors.

In FIG. 1 is shown a first electrode 10 with a carrier sheet 11 and three sensors 12, 13, 14 on one side of the carrier sheet, which is preferably of a flexible material. The sheet 11 has an L-shaped contour. The three sensors have a size of a few mm in diameter, and they can be of any suitable type such as Ag/AgCl. The electrode has a suitable adhesive for attaching the electrode to the skin of an animal or human being, and an electrically conductive medium such as a gel at each of the sensors for creating electrical contact between the sensors and the skin. A straight line between the centres of the sensors 12 and 13 is perpendicular to a straight line between the centres of the sensors 13 and 14. The two sensors 12 and 13 can be used as one pair of sensors, and the two sensors 13 and 14 can be used as another pair of sensors, where the sensor 13 is common to both pairs. Conductors can be connected to each of the sensors in any suitable manner such as the snap type.

Figure 2:
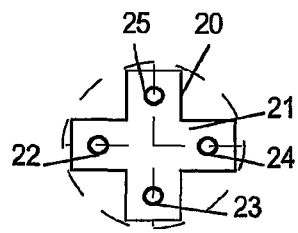
FIG. 2 shows an electrode like that in FIG. 1 but with four sensors.

In FIG. 2 is shown a second electrode 20 of similar construction with a carrier sheet 21 and four sensors 22, 23, 24 and 25. The sheet 21 has a cruciform contour. A straight line between the centres of the sensors 22 and 24 is perpendicular to a straight line between the centres of the sensors 23 and 25. The two sensors 22 and 24 can be used as one pair of sensors, and the two sensors 23 and 25 can be used as another pair of sensors, so that none of the sensors is common to both pairs.

Figure 3:
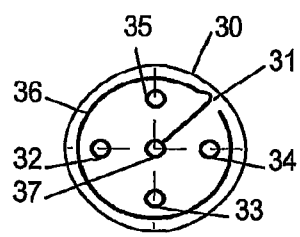
FIG. 3 shows an electrode like that in FIG. 4 with four sensors and a conductor strip for use as an antenna.

In FIG. 3 is shown a third electrode 30 of similar construction as the electrode 20 and has a carrier sheet 31 and four sensors 32, 33, 34 and 35 on the carrier sheet. The carrier sheet 31 has a circular contour. In addition the electrode 30 has an electrically conducting strip 36 applied to the sheet and a terminal 37 for connecting the strip 36 to external equipment for receiving signals from the external equipment to be wirelessly transmitted by the electrically conducting strip, which then acts as a transmitting antenna, as will be explained further below. The antenna 36 and its connector 37 are insulated such as not to come into electrical contact with the patient's skin, when the electrode is attached to a patient. The antenna can have any other suitable form than the one shown.

Figure 4:
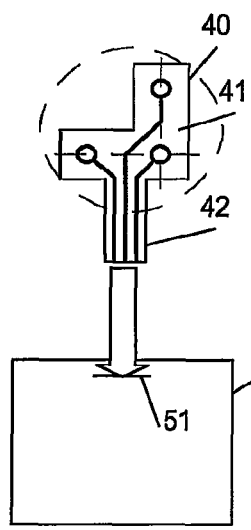
FIG. 4 shows an electrode with three sensors and an edge connection to the individual sensors, with the edge connector connectable to a wireless transmitter.

In FIG. 4 is shown an electrode 40 of similar construction to that of the electrode 10 in FIG. 1. The carrier sheet 41 of the electrode 40 has a tongue 42 extending from an edge of the sheet. Electrical conductor strips on the sheet extend from each of the sensors to the tongue, where at least an end portion of each conductor is exposed, so that electrical contact can be obtained to each of the sensors.

In FIG. 4 is also shown a wireless transmitter 50 with an opening in the form of a slit 51 for receiving the tongue 42 of the electrode 40. The transmitter 50 has contacts (not shown but known as such) for establishing electrical contact with the corresponding contacts on the tongue 42 of the electrode 40.

Figure 5:
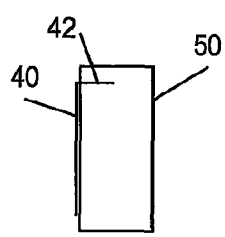
FIG. 5 shows the electrode connected to the transmitter in FIG. 4.

FIG. 5 is a side view of the transmitter 50 with the tongue 42 inserted in the slit, and the electrode 40 is folded to lie close to a side face of the transmitter, where it is preferably secured by means of an adhesive. The exposed side of the electrode has an adhesive or other suitable means for detachably attaching the electrode to the skin of a patient with the sensors in electrical contact with the skin. In the shown configuration the electrode 40 and the transmitter 50 are thus suited for being attached to the skin of the patient.

Figure 6:
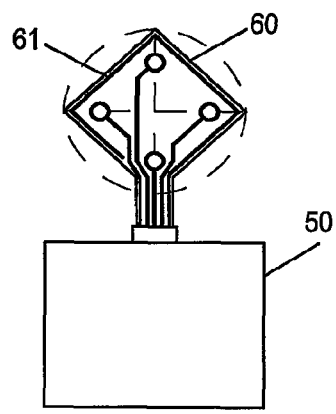
FIG. 6 shows an electrode with four sensors and a conductor strip for use as an antenna, and connected to a wireless transmitter.

In FIG. 6 is shown an electrode 60 of similar construction to that of the electrode 40 in FIG. 4. However, the sheet has a further conductor strip 61 extending along the periphery of the sheet and connected to the transmitter 50, so that the conductor strip 61 is a transmitting antenna that can receive electrical signals from the transmitter 50 to be wirelessly transmitted by the conductor strip 61 acting as an antenna.

In the embodiments in FIGS. 4 and 6 the electrical conductor strips on the carrier including the antenna conductor strip 61 are insulated so as not to come into electrical contact with the patient's skin, when the electrodes are attached to the skin of a patient.

Figure 7:
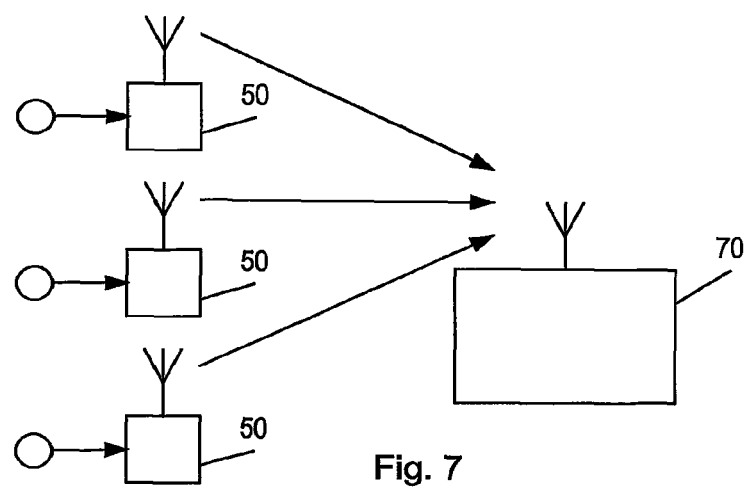
FIG. 7 shows a system with a plurality of electrodes connected to individual wireless transmitters and a receiver receiving signals transmitted from the transmitters.

In FIG. 7 is shown a system with a plurality of electrodes connected to individual wireless transmitters 50 and a wireless receiver 70 receiving signals transmitted from the transmitters. The electrodes and transmitters can be attached to the skin of a patient at predetermined locations. The transmitters transmit signals representing the sensed potentials, and the receiver 70 receives the signals transmitted from all the transmitters.

The skilled person such as a physician or a medical assistant, who attaches e.g. traditional ECG electrodes with a single sensor to a patient, will attach the electrodes at predetermined locations identified in relation to the patient's anatomy. These locations are determined with an accuracy that allows comparison of repeated measurements performed on the same patient and of measurements taken on different patients. Repeated measurements on the same patient can e.g. be performed with short or long intervals between them and possibly also by a different staff. Measurements taken on different patients are used e.g. for statistical purposes. In order to ensure a high diagnostic value it is important that the electrodes are attached at the predetermined locations with a high accuracy every time, i.e. within prescribed limits identified in relation to the patient's anatomy and with usual skilled human accuracy.

The electrodes of the invention therefore have a size small enough so that the sensors are all within an area that can be covered by an electrode with a single sensor, which is normally used for sensing the electrical potentials on patients. The electrodes have a size that allows a plurality of the electrodes to be attached to the skin of a patient at respective locations normally used for sensing the electrical potentials, without any of the electrodes overlapping each other. In practice this means that the sensors are all within the periphery of a circle with a diameter of 70 mm or less. In FIGS. 1, 2, 4 and 6 such a circle is indicated by a dashed circle, and the circular electrode in FIG. 3 is also within the periphery of such a circle.

FUNCTION OF THE INVENTION

Figure 8:
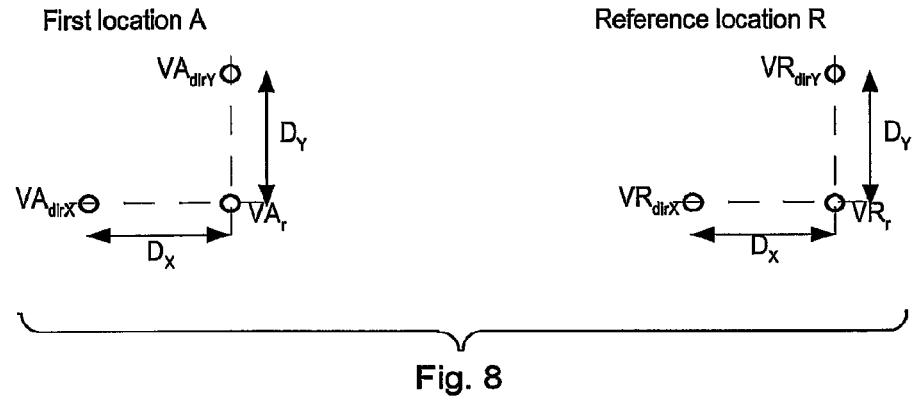
FIG. 8 illustrates the measuring principle of the invention.

The operator attaches an electrode of the invention at each of the locations traditionally chosen by the operator of ECG equipment for attaching an electrode with a single sensor point. The operator also attaches a wireless transmitter 50 thereto if the wireless transmitter is not an integral part of the electrode. This is illustrated in FIG. 8, where one location is chosen as a reference location R and one location is chosen as a first location A. The method according to one aspect of the invention describes a method to determined or estimate the electrical potentials at the first location A with reference to the reference location R. Usually, electrodes will be attached at several further locations, in which the electrical potentials are to be determined with reference to the reference location R, but for simplicity only one such location A is shown in FIG. 8.

For example, in the measurement of Lead I in a standard ECG measurement, two electrodes are used, one at the right arm and one at the left arm. The right arm location would the be the first location A discussed above and the left arm location would be the reference location R discussed above. For the measurement of Lead II in a standard ECG measurement, two electrodes are used, one at the right arm (first position A) and one at the left leg (reference position R). And for the measurement of Lead III, again two electrodes are used, one at the left arm (first position A) and one at the left leg (reference position R).

Once the electrodes have been attached to the body, in a first embodiment of a method according to the invention the following is performed at the first location A:

an electrical potential ($VA_r$) is sensed in a first reference position, an electrical potential ($VA_{dirX}$) is sensed in a position in a first direction from the first reference position, a first electrical potential difference ($VA_{dirX}$)−($VA_r$) between the electrical potential ($VA_{dirX}$) in the position in the first direction from the first reference position and the electrical potential ($VA_r$) in the first reference position is determined, signals representing the first electrical potential difference are transmitted, an electrical potential ($VA_{dirY}$) is sensed in a position in a second direction from the first reference position, a second electrical potential difference ($VA_{dirY}$)–($VA_r$) between the electrical potential ($VA_{dirY}$) in the second direction from the first reference position and the electrical potential ($VA_r$) in the first reference position is determined, and signals representing the second electrical potential difference are transmitted.

At each of the further locations and at the reference location R corresponding operations are performed. The receiver receives the transmitted signals, and the electrical potential of the first location (A) relative to the reference location (R) is determined as the difference between a size of a first vector defined by the first and second electrical potential differences and a size of a reference vector defined by the third and fourth electrical potential differences.

In another embodiment of the invention the electrodes are arranged such that the linearly independent directions of the electrode at the first location are substantially the same as the linearly independent directions of the electrode at the reference location and the following is performed at the first location A:

an electrical potential ($VA_r$) is sensed in a first reference position, an electrical potential ($VA_{dirX}$) is sensed in a position in the X-direction from the first reference position, a first electrical potential difference ($VA_{dirX}$)–($VA_r$) is determined between the electrical potential ($VA_{dirX}$) in the X-direction from the first reference position and the electrical potential ($VA_r$) in the first reference position, signals representing the first electrical potential difference are transmitted, an electrical potential ($VA_{dirY}$) is sensed in a position in the Y-direction from the first reference position, a second electrical potential difference ($VA_{dirY}$)–($VA_r$) is determined between the electrical potential ($VA_{dirY}$) in the Y-direction from the first reference position and the electrical potential ($VA_r$) in the first reference position, signals representing the second electrical potential difference are transmitted.

At each of the further locations and at the reference location R corresponding operations are performed. The receiver receives the transmitted signals, and the electrical potential of the first location (A) relative to the reference location (R) is determined as the sum of a first difference between the first electrical potential difference and the third electrical potential difference and a second difference between the second electrical potential difference and the fourth electrical potential difference.

In the preferred embodiment wireless transmission is preferred, but wired transmission through electrical conductors is also usable.

FIG. 8 illustrates the basic concept of the invention of monitoring the biopotential as a difference between two sensor points of an electrodes spaced a known distance, $D_X$ and $D_Y$ respectively, apart. This is done in two linearly independent directions X, Y preferably perpendicular to each other. Electrodes of the invention are attached to a first location A and at a reference location R, respectively. At the first location A the potential difference at each pair of sensors is measured as the electrical potential difference between the local reference electrode ($V_r$) and each of the directional electrodes ($VA_{dirX}$ or $VA_{dirY}$) giving:

$$VA_X = VA_{dirX} - VA_r$$

$$VA_Y = VA_{dirY} - VA_r$$

When the two linearly independent directions defined by lines through the centres of respective pairs of sensors are perpendicular to each other the length or size of the signal in two dimensions can be calculated as:

$$V_{signal} = \sqrt{VA_{dirX}^2 + VA_{dirY}^2}$$

In the case where the sensor points are far from each other with respect to the length of the signal passing under the electrode, this magnitude is proportional to the total size of the signal passing under the electrode. Furthermore, not only the size of the total signal can be used in identifying the physiological function, but also the direction from where the signal originated can be determined in relation to the location of the electrode, e.g. if the signal is travelling to or away from the electrode and in which direction. However, if the direction information is to be used, it is important that the orientation of the electrode is known.

The resulting total size of the signal, e.g. the length of the sum of the two directional vectors has no information about the direction of the travelling signal. When calculating the resulting ECG leads from the magnitudes of the vectors measured by the electrodes located at each of the three limb positions the result will simulate an absolute value of the traditional ECG lead (I, II, III). In this particular case, where the direction information of the vectors are not used, the orientation of the electrodes of the invention need not be known. This reduces the requirements for proper orientation of the electrodes when they are mounted on the body.

If it is desired to know the direction of travel of the signal, the orientation of the electrodes of the invention must be known. The electrode 40 in FIG. 4 is particularly suited for this since it is provided with a tongue 42 which acts as a visual indication of the orientation of the electrode. The electrode can then be placed with its tongue 42 extending in a predetermined direction, e.g. up or down. In other cases, the electrode could be provided with visual indication means which include a reference to an anatomical feature of the body. For example, the electrodes could be provided with a diagram of a body. The orientation of the electrode could then be arranged such that the diagrammed body is oriented the same as the body of the patient on which the electrode is mounted. In this way, even for non skilled personnel, it is easy to mount the electrodes properly with no possibilities of mistakes.

The electrodes of the invention are placed like traditional ECG electrodes in standardised locations on the skin of a patient. The electrodes record the signals in the x and y directions and transmit the two signals as a difference signal between the common reference point and the recording electrode to a monitor connected to the receiver. This results in a locally referenced signal that can be transmitted wirelessly using conventional RF technology or digital transmitting technology (e.g. Bluetooth, Zigbee, WIFI, WLAN, etc.) or other suitable wireless transmission means. This results in 2 signals for each electrode, hence 6 signals from 3 electrodes to perform a normal 3 lead ECG deviation. When the signals have been transmitted the signals can be transformed into the traditional ECG lead.

Two basic types of methods of transforming the sensed potential differences into traditional ECG leads (e.g. I, II, III, aVR, aVL, aVF) are contemplated as described below. The first type of method is based on vector magnitudes. However, it has been discovered, that methods of estimating the standard ECG leads based on electrodes as described in this specification can be improved by taking the directional information of the potential into account. The second type of method is therefore based on the separate vector components of the vectors of the measured potential differences. In the first type of method, the orientation of the sensors is not as important. In the second type of method, the orientation of the sensors is import.

1. Limb leads based on the length of each difference.

A method based on raw signal lengths:

e.g. $I = \sqrt{VA_{dirX}^2 + VA_{dirY}^2} - \sqrt{VR_{dirX}^2 + VR_{dirY}^2}$

A method based on time-integrated signal lengths:

e.g. $I = \sqrt{(\int VA_{dirX})^2 + (\int VA_{dirY})^2} - \sqrt{(\int VR_{dirX})^2 + (\int VR_{dirY})^2}$ A method based on time-integrated vector magnitudes:

e.g. $I = \int\sqrt{(VA_{dirX})^2 + (VA_{dirY})^2} - \int\sqrt{(VR_{dirX})^2 + (VR_{dirY})^2}$ 2. Limb leads based on the directional size of the differences.

A method based on same orientation/direction of the electrodes:

e.g. $I = \dfrac{(VA_{dirX} - VR_{dirX}) + (VA_{dirY} - VR_{dirY})}{gain}$

A method based on integration of the electrode directional size:

e.g. $I = \dfrac{\left(\int VA_{dirX} - \int VR_{dirX}\right) + \left(\int VA_{dirY} - \int VR_{dirY}\right)}{gain}$ A method based on mean filtering of the directional size:

e.g. $I = \dfrac{\left(\overset{\Delta t}{mean}(VA_{dirX}) - \overset{\Delta t}{mean}(VR_{dirX})\right) + \left(\overset{\Delta t}{mean}(VA_{dirY}) - \overset{\Delta t}{mean}(VR_{dirY})\right)}{gain}$ Corresponding calculations can be made to obtain each of the other ECG leads II, III, aVR, aVL and aVF.

The gain in the above formulas can usually be set to unity (1). This is true since in most cases, the actual magnitude of the ECG signal is not critical, rather it is the overall shape and timing of the ECG signal which is relevant. Therefore, the gain can be neglected in most cases.

Figure 9:
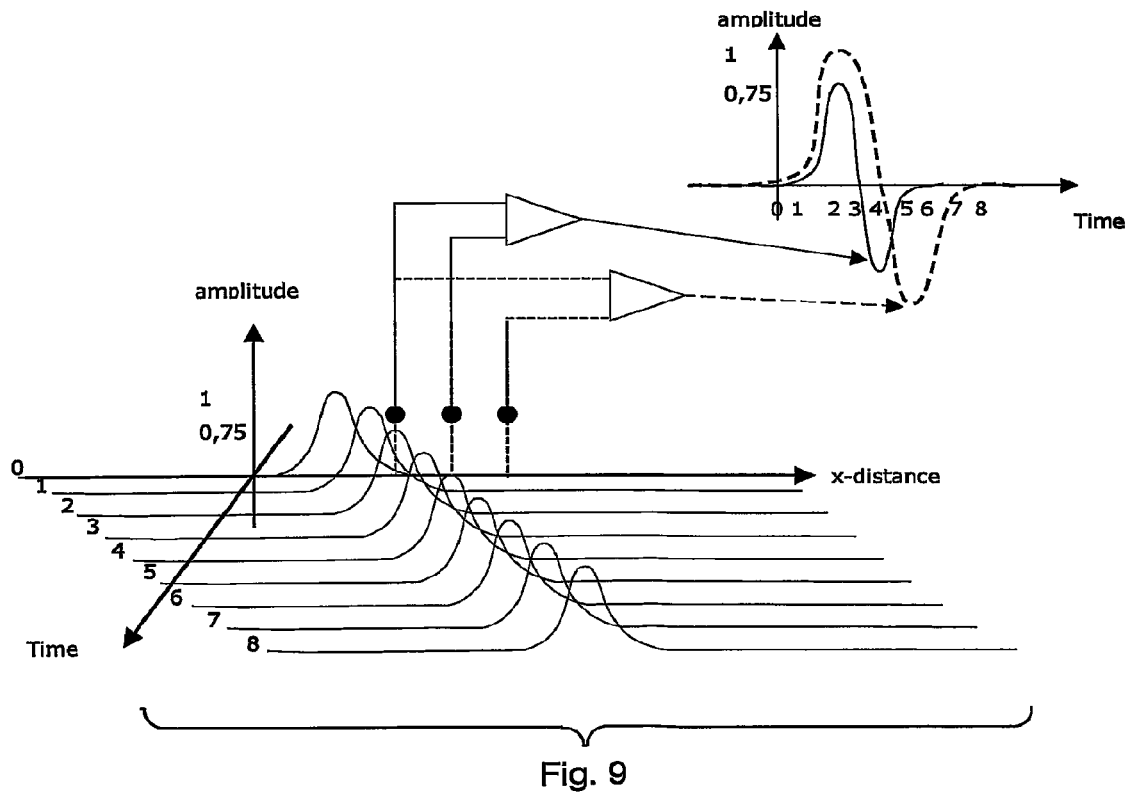
FIG. 9 illustrates the effect of changing the spacing between the sensor points on the electrode.

The different methods above can be used in different circumstances. As mentioned previously, the spacing of the sensors on each electrode has an effect on the signal which is measured. The effect of the spacing can be seen in FIG. 9. When the spacing is larger than the signal length, then the difference measurement between the two sensors is a good representation of the actual signal passing underneath the electrode. If the spacing is larger than the signal length, then the difference measurement between the two sensors becomes a differential of the signal passing the sensors.

Since the length of the signal is different in different people depending on different characteristics of the body, the signal should be interpreted differently for different people. For example, if the person being examined has a relatively fast signal, then the signal passing underneath the sensors will be relatively short and the entire signal will fit between the sensors. In this case, the difference signal is representative of the actual signal underneath the sensors. In this case, the type of method used would be the type which is based on instantaneous signals. However, if the person being examined has a relatively slow signal, then the signal passing underneath the sensors will be relatively long and only a portion of the signal will fit between the sensors. In this case, the difference measured by the electrode will be more representative of a derivative. Therefore in this case, the type of method used will be the type using an integration.

In certain cases, it could be imagined that a combination of different methods could be used. For example, a method based on instantaneous signals could be combined with a method based on integration. The two calculations could be combined in many different ways. One example is a linear combination of a result from a method based on instantaneous signals ($S_{inst}$) and a result based on integrated signals ($S_{int}$).

$$S = K S_{inst} + (1-K) S_{int}$$

In this case, K is a constant between 0 and 1. In the case where more emphasis is to be placed on the integrated data, K would be small. In the case where more emphasis is to be placed on the instantaneous data, K would be large. It could also be imagined that K is a function of time, where different signals are weighted more heavily at different points in time.

One way of choosing the best method for a particular situation is to compare the resulting ECG signal calculated with the above methods with the simultaneously recorded "real" ECG derivatives. For example, an electrode according to the current specification could be attached at a location as well as a traditional electrode. The traditional electrode could be used for "tuning" the method used to calculate the result based on the signals measured by the electrode according to the current specification. For comparison of the similarity of the limb leads obtained with the method of the invention to the traditional limb leads the correlations coefficients ($r_{XY}$) of simultaneous recordings were calculated.

Cross-Correlation Function:

$$R_{XY}(t_1, t_2) \triangleq E\{X^*(t_1) Y(t_2)\}$$

Cross-Covariance Function:

$$C_{XY}(t_1, t_2) \triangleq R_{XY}(t_1, t_2) - \mu_X^*(t_1)\mu_Y(t_2)$$

Correlation Coefficient:

$$r_{XY}(t_1, t_2) \triangleq \dfrac{C_{XY}(t_1, t_2)}{\sqrt{C_{XX}(t_1, t_2) C_{YY}(t_1, t_2)}}$$

The correlation coefficient can be used to evaluate the similarity between two linear dependent signals. Generally speaking the correlation coefficient will be equal to 1 when the signals are identical, and −1 when the signals are inverted relative to each other. The correlation coefficient be thus could used as a measure of similarity.

REFERENCES

[1] Erwin Kreyszig, "Advanced Engineering Mathematics", 1993, 7th ed., John Wiley & sons, Inc. New York. ISBN: 0-471-59989-1

[2] Erik Sandøe, Bjarne Sigurd, "Arrhythmia Diagnosis and management", 1984, Fachmed AG, Germany, ISBN: 3-905 598-00-0

[3] R. F. Schmidt, "Fundamentals of Neurophysiology", 1981, 3rd ed, Springer Verlag, New York, ISBN: 0-387-96147-x

[4] S. Grimmes, Ø. G. Martinsen "Bioimpedance & Bioelectricity", 2000, Academic Press, London, ISBN: 0-12-303260-1

[5] John G. Webster, "Medical instrumentation, Application and design", 1998, 3rdh ed. John Wiley & sons Inc. ISBN: 0-471-15368-0

[6] Josephe D. Bronzino, "The Biomedical Engineering Handbook", 1995, CRC Press Inc., ISBN: 0-8493-8346-3

[7] F. B. Sachse, C. D. Werner, K. Meyer-Waarden, O. Dösse, "Applications of the Visible Man Dataset in Electrocardiology: Calculation and Visualization of Body Surface Potential Maps of a Complete Heart Cycle", The National Library of Medicine, http://www.nlm.nih.gov/research/visible/vhpconf98/AUTHORS/SACHSE 2/sachse2.htm

[8] "Electrode Placement Guide", Cardiology, 2003, AMBU A/S

[9] K. Sam Shanmugan, A. M. Breipohl "Random signals", 1988, John Wiley Sons Inc. New York, ISBN:0-471-61274-x [10] Einthoven W. "The different forms of the human electrocardiogram and their signification.", Lancet 1912(1): 853-861.

The invention claimed is:

1. A method of determining the electrical potential of a first location (A) on skin of an animal or human being relative to a reference location (R) on the skin of an animal or human being, the method comprising the steps of:
    attaching, to each of the first location (A) and the reference location (R) an electrode, each electrode having at least three sensors arranged so that lines through centers of respective pairs of sensors define two linearly independent directions, and where the electrode attached at the first location and the electrode attached at the reference location are oriented such that the two linearly independent directions defined by the electrode at the first location (A) are substantially the same as the two linearly independent directions of the electrode at the reference location (R), each electrode being connected to a wireless transmitter that is adapted to receive sensed electrical potential and to transmit signals representing the sensed electrical potentials;
    sensing, with each of the sensors on each electrode: an electrical potential on the skin;
    transmitting, using each respective wireless transmitter, signals representing at least two differences between pairs of potentials sensed with corresponding pairs of sensors on each electrode;
    receiving, using a wireless receiver, the transmitted signals; and
    determining the electrical potential at the first location (A) relative to the reference location (R) based on the received signals.

2. A method according to claim 1 further comprising determining parameters representing an instantaneous amplitude of a bioelectrical field in the animal or human being.

3. A method according to claim 1 further comprising determining parameters representing a polarity of a bioelectrical field in the animal or human being.

4. A method according to claim 1 further comprising determining parameters representing a direction of propagation of a bioelectrical field in the animal or human being.

5. A method of determining electrical potential at a first location (A) relative to a reference location (R) on skin of an animal or human being, the method comprising.
    attaching to each of the first (A) and reference (R) locations an electrode having at least three sensors arranged so that lines through centers of respective pairs of sensors define two linearly independent directions, such that the electrode attached at the first location and the electrode attached at the reference location are oriented such that the two linearly independent directions defined by the electrode at the first location (A) are substantially the same as the two linearly independent directions of the electrode at the reference location (R), the electrode attached at the first location and the electrode attached at the reference location being connected to a first wireless transmitter and a second wireless transmitter, respectively, that are adapted to receive sensed electrical potential and to transmit signals associated with the sensed electrical potentials;
    at the first location (A):
    sensing an electrical potential ($VA_r$) in a first reference position,
    sensing an electrical potential ($VA_{dirX}$) in a position in a first direction from the first reference position,
    determining, using the first wireless transmitter, a first electrical potential difference ($VA_{dirX}$)−($VA_r$) between the electrical potential ($VA_{dirX}$) in the position in the first direction from the first reference position and the electrical potential ($VA_r$) in the first reference position,
    sensing an electrical potential ($VA_{dirY}$) in a position in a second direction from the first reference position,
    determining, using the first wireless transmitter, a second electrical potential difference ($VA_{dirY}$)−($VA_r$) between the electrical potential ($VA_{dirY}$) in the second direction from the first reference position and the electrical potential ($VA_r$) in the first reference position,
    transmitting, using the first wireless transmitter, signals representing the first and second electrical potential difference:
    at the reference location (R):
    sensing an electrical potential ($VR_r$) in a second reference position,
    sensing an electrical potential ($VR_{dirX}$) in a position in a third direction from the second reference position,
    determining, using the second wireless transmitter, a third electrical potential difference ($VR_{dirX}$)−($VR_r$) between the electrical potential ($VR_{dirX}$) in the third direction from the second reference position and the electrical potential ($VR_r$) in the second reference position,
    sensing an electrical potential ($VR_{dirY}$) in a position in a fourth direction from the second reference position,
    determining, using the second wireless transmitter, a fourth electrical potential difference ($VR_{dirY}$)−($VR_r$) between the electrical potential ($VR_{dirY}$) in the fourth direction from the second reference position and the electrical potential ($VR_r$) in the second reference position,
    transmitting, using the second wireless transmitter, signals representing the third and fourth electrical potential difference,
    receiving, using a wireless receiver, the transmitted signals, and determining the electrical potential of the first location (A) relative to the reference location (R) based on the first, second, third and fourth electrical potential differences.

6. A method according to claim 5 wherein the electrical potential of the first location (A) relative to the reference location (R) is based on a difference between a size of a first vector defined by instantaneous first and second electrical potential differences and a size of a reference vector defined by instantaneous third and fourth electrical potential differences.

7. A method according to claim 5 wherein the electrical potential of the first location (A) relative to the reference location (R) is based on a difference between a size of a first vector defined by integrated first and second electrical potential differences and a size of a reference vector defined by integrated third and fourth electrical potential differences.

8. A method according to claim 5 wherein the electrical potential of the first location (A) relative to the reference location (R) is based on a difference between a time integrated magnitude of a first vector defined by the first and second electrical potential differences and a time integrated magnitude of a reference vector defined by the third and fourth electrical potential differences.

9. A method according to claim 5, characterized in that the electrical potential of the first location (A) relative to the reference location (R) is determined as a sum of a first difference between the first electrical potential difference and the third electrical potential difference and a second difference between the second electrical potential difference and the fourth electrical potential difference.

10. A method according to claim 5, characterized in that the electrical potential of the first location (A) relative to the reference location (R) is determined as a sum of a first difference between an integration of the first electrical potential difference and an integration of the third electrical potential difference and a second difference between an integration of the second electrical potential difference and an integration of the fourth electrical potential difference.

11. A method according to claim 5, characterized in that the electrical potential of the first location (A) relative to the reference location (R) is determined as a sum of a first difference between a moving average of the first electrical potential difference and a moving average of the third electrical potential difference and a second difference between a moving average of the second electrical potential difference and a moving average of the fourth electrical potential difference.

* * * * *